United States Patent
Greager et al.

(10) Patent No.: US 11,572,512 B2
(45) Date of Patent: Feb. 7, 2023

(54) GASIFICATION PROCESS

(71) Applicant: Velocys Technologies Ltd, Oxford (GB)

(72) Inventors: Ivan Greager, Houston, TX (US); Roger Harris, Houston, TX (US); Rudolph Havenga, Berkshire (GB); Neil King, Oxford (GB)

(73) Assignee: Velocys Technologies Ltd., Oxford (GB)

( * ) Notice: Subject to any disclaimer, the term of this patent is extended or adjusted under 35 U.S.C. 154(b) by 0 days.

(21) Appl. No.: 17/499,408

(22) Filed: Oct. 12, 2021

(65) Prior Publication Data

US 2022/0112429 A1 Apr. 14, 2022

Related U.S. Application Data

(60) Provisional application No. 63/091,685, filed on Oct. 14, 2020.

(30) Foreign Application Priority Data

Nov. 18, 2020 (GB) ...................................... 2018119

(51) Int. Cl.
*C10G 2/00* (2006.01)
*C10G 47/00* (2006.01)
(Continued)

(52) U.S. Cl.
CPC .................. *C10G 2/31* (2013.01); *C01B 3/24* (2013.01); *C10G 45/58* (2013.01); *C10G 47/00* (2013.01);
(Continued)

(58) Field of Classification Search
CPC .. C10G 2/32; C01B 3/586; C01B 3/12; C01B 3/382; C01B 3/36; C01B 2203/06;
(Continued)

(56) References Cited

U.S. PATENT DOCUMENTS 10,633,594 B1 4/2020 Wright
2006/0211777 A1 9/2006 Severinsky
(Continued)

FOREIGN PATENT DOCUMENTS

CA 2759009 10/2010
CN 109321279 A 2/2019
(Continued)

OTHER PUBLICATIONS

DE 10201301266 A1 machine translation, Feb. 2015.*
(Continued)

*Primary Examiner* — Jafar F Parsa
(74) *Attorney, Agent, or Firm* — Renner, Otto, Boisselle & Sklar, LLP (57) ABSTRACT

An integrated process for the production of a useful liquid hydrocarbon product comprises: feeding a gasification zone with an oxygen-containing feed and a first carbonaceous feedstock comprising waste materials and/or biomass, gasifying the first carbonaceous feedstock in the gasification zone to produce first synthesis gas, partially oxidising the first synthesis gas in a partial oxidation zone to generate partially oxidised synthesis gas, combining at least a portion of the first synthesis gas and/or the partially oxidised synthesis gas and at least a portion of electrolysis hydrogen obtained from an electrolyser in an amount to achieve the desired hydrogen to carbon monoxide molar ratio of from about 1.5:1 to about 2.5:1, and to generate a blended synthesis gas, wherein the electrolyser operates using green electricity; and subjecting at least a portion of the blended synthesis gas to a conversion process effective to produce the liquid hydrocarbon product.

20 Claims, 1 Drawing Sheet

(51) Int. Cl.
  *C10G 45/58* (2006.01)
  *C25B 1/04* (2021.01)
  *C25B 9/17* (2021.01)
  *C01B 3/24* (2006.01)

(52) U.S. Cl.
  CPC .............. *C25B 1/04* (2013.01); *C25B 9/17* (2021.01); *C01B 2203/0205* (2013.01); *C01B 2203/025* (2013.01); *C01B 2203/04* (2013.01); *C01B 2203/062* (2013.01); *C10G 2300/1003* (2013.01); *C10G 2300/1011* (2013.01); *C10G 2300/1022* (2013.01); *C10G 2400/04* (2013.01); *C10G 2400/08* (2013.01)

(58) Field of Classification Search
  CPC .......... C01B 2203/062; C01B 2203/14; C01B 2203/0283; C01B 2203/061; C07C 29/1518; C07C 31/04
  See application file for complete search history.

(56) References Cited

U.S. PATENT DOCUMENTS

| | | | |
|---|---|---|---|
| 2015/0152562 A1 | 6/2015 | Bernical | |
| 2020/0017422 A1 | 1/2020 | Kramer et al. | |
| 2022/0081289 A1* | 3/2022 | De Sarkar | ............... C01B 3/36 |

FOREIGN PATENT DOCUMENTS

| | | |
|---|---|---|
| EP | 2350233 B1 | 9/2020 |
| JP | 2018002751 A | 1/2018 |
| WO | 2008033812 A1 | 3/2008 |
| WO | 2010060236 A1 | 6/2010 |
| WO | 2013064552 A1 | 10/2013 |
| WO | 2013152903 A1 | 10/2013 |
| WO | 2015014459 A1 | 2/2015 |
| WO | 2017029189 A1 | 2/2017 |
| WO | 2018026388 A1 | 2/2018 |
| WO | 2018078661 A1 | 5/2018 |

OTHER PUBLICATIONS

Loewert, Marcel et al; "Dynamically Operated Fischer-Tropsch Synthesis in PtL—Part 2: Coping with Real PV Profiles", Chemengineering, vol. 4, No. 2, Jun. 13, 2020, p. 27.

Gruber, Hannes et al; "Fischer-Tropsch products from biomass-derived syngas and renewable hydrogen", Biomass Conversion and Biorefinery, Springer Berlin Heidelberg, Berlin/Heidelberg, vol. 11, No. 6, Jun. 22, 2019, pp. 2281-2292.

Seiler, Jean-Marie et al; "Technical and economical evaluation of enhanced biomass to liquid fuel processes", Energy, vol. 35, No. 9, Sep. 1, 2010, pp. 3587-3592.

International Search Report and Written Opinion for related International Application No. PCT/EP2021/077949 dated Jan. 4, 2022.

Combined Search and Examination Report for related Great Britain Application No. GB2018119.4 dated Jan. 8, 2021.

* cited by examiner

GASIFICATION PROCESS

This application claims the benefit of U.S. Provisional Patent Application No. 63/091,685, filed Oct. 14, 2020, and claims priority to UK Patent Application No. GB 2018119.4, filed Nov. 18, 2020, the disclosures of which are incorporated herein by reference in their entireties.

TECHNICAL FIELD

The present invention concerns a gasification process for the production of products such as higher molecular weight (typically liquid) hydrocarbon products, for example synthetic fuels, from waste materials and/or biomass materials in combination with electrolysis hydrogen generated from an electrolyser in a manner which allows increased control over obtaining the desired molar ratio of hydrogen to carbon monoxide of a specific process in comparison with conventional processes of the type. The gasification process of the invention may also be used in the production of separation products such as hydrogen.

BACKGROUND

It is widely known in the art to manufacture useful products such as synthetic fuels from waste materials and/or biomass and/or gaseous material, such as natural gas. We may refer to such manufacturing methods as WTL (Waste-to-Liquids), BTL (Biomass-to-Liquids) and GTL (Gas-to-Liquid) processes.

Typical WTL and BTL processes involve several reactions, for example, the gasification of waste or biomass feedstock by steam reforming processes and/or partial oxidation and/or water gas shift reaction and/or de-volatilization and/or carbon dioxide reforming and/or methanation, to produce a raw synthesis gas which may then be treated and purified in various ways before entering a chemical reaction train to generate a useful product.

Typical GTL processes involve the gasification by steam methane reforming and/or autothermal reforming of natural gas feedstock to produce a raw synthesis gas which may then be treated and purified in various ways before entering a chemical reaction train to generate a useful product.

Additionally, it is widely known in the art to generate hydrogen through the electrolysis of water. Typical electrolysis processes involve the decomposition of water into oxygen and hydrogen gas by passing an electric current through the water.

In the case of the useful product being a synthetic fuel (for example a drop-in synthetic fuel), the chemical reaction train will typically comprise a Fischer-Tropsch (FT) reactor. The FT process is widely used to generate fuels from carbon monoxide and hydrogen and can be represented by the equation:

$(2n+1)H_2 + nCO \rightarrow C_nH_{2n+2} + nH_2O$

For an FT process the usage ratio approximates ideally to 2 when n is a large number in the above equation. For example, when n=100 the ratio is 2.01. It will be appreciated that in a complex reaction network, side reactions may occur in which case the overall usage ratio and the primary reaction stoichiometry may not be synonymous and further both of these can be different from the ratio of reactants made available for the reaction. For example, in the case of FT the usage ratio in reality is typically in the range of 1.95 to 2.05, while the $H_2$:CO ratio in the feed can vary significantly.

To date, there appears to have been little consideration given as to how the feed $H_2$:CO ratio may be controlled to reduce environmental impact, increase efficiency, improve profitability and reduce complexity in an otherwise satisfactory WTL, BTL or GTL process.

The term "Carbon Intensity" or "CI" may also be construed in accordance with a model based on an overall lifecycle assessment, for example forest to tailpipe. For example, GREET a publicly available spreadsheet model developed at Argonne National Laboratory (ANL) or a California-specific version of Argonne National Laboratory's GREET life cycle model used to calculate GHG emissions under the California Low Carbon Fuel Standard (LCFS) is the CA-GREET Version 3.0 (Tier 1) model. Other appropriate models are available such as the Biomethane & Biogas Carbon Calculator published by NNFCC Ltd, Biocentre, York Science Park, Innovation Way, York, YO10 5NY UK. Carbon intensity provides a measure of the overall energy efficiency of a process. Carbon intensity may be understood for example in terms of grams of CO2 equivalent to per MJ of fuel produced.

It would be desirable to allow greater control of carbon intensity when obtaining the desired $H_2$:CO molar ratio in a chemical engineering process for the production of useful products, for example synthetic fuels, from a wide range of different carbonaceous feedstocks and energy sources. In particular, it would be beneficial to afford a more environmentally beneficial process, such as that through the use of clean power and a process which is able to be flexibly responsive to a wide variety of feedstock, most desirably, renewable feedstock.

The current environmental standards target in the US is that for an advanced biofuel produced in a WTL or BTL process to qualify for RINs (renewable identification number), a 60% or greater reduction in greenhouse gas emissions (measured as gCO2-eq/MJ of fuel) is achieved compared to the baseline for a fuel derived from a refinery. Similarly, the Renewable Transport Fuel Obligation Guidance issued by the UK government (Article 17(2)) currently mandates GHG emissions savings of at least 60%. Operationally it may be desirable to reduce the greenhouse gas emissions of any given synthetic fuel production pathway by at least 65%.

The invention is concerned particularly but not exclusively with the integration of a gasification process utilising waste and/or biomass materials as the feedstock, with an electrolysis process utilising a renewable electricity source and optionally a gasification process utilising gaseous materials, more preferably renewable natural gas.

WTL, BTL and GTL processes are very well known in the art.

For example EP2350233A1 relates to a method for producing liquid hydro carbonaceous product from solid biomass, the method comprising gasifying solid biomass to produce raw synthesis gas, conditioning the raw synthesis gas to obtain purified synthesis gas and subjecting the purified gas to a Fischer-Tropsch synthesis.

WO2018026388 describes converting one or more carbon-containing feedstocks, for example plastics, agriculture residues, and forest remediation wood into hydrocarbons.

US10633594B1 describes converting natural gas to liquid fuels such as kerosene, diesel or jet fuel wherein the GTL process has two main steps: (1) the generation of the synthesis gas (syngas), and (2) the conversion of the synthesis gas into liquid fuels, such as kerosene and diesel.

Some prior art WTL, BTL and GTL processes have sought integration with additional processes, such as electrolysis.

CA2759009 describes a process and system for producing synthesis gas (syngas) by combining hydrogen and carbon monoxide from separate sources while controlling the mole ratio ($H_2/CO$) of the syngas product and wherein the hydrogen is produced by splitting water.

US2006211777 describes an apparatus and a method to convert electric energy into hydrocarbon compound fuels.

US2020017422 describes a gasification processes for the production of renewable natural gas (RNG), with such processes being integrated with electrolysis for supplying oxygen and hydrogen feeds.

Other prior art processes discuss electrolysis in some capacity.

CN109321279 describes an adjusting system and adjusting method of coal-formed synthesis gas, comprising a coal gasifying unit used for gasifying coal.

WO2010060236 describes a method for producing methanol, in which oxygen is employed as gasification agent for the gasification of coal.

WO2017029189 describes a system for producing fuel and thermal energy, comprising an electrolyser for producing oxygen and hydrogen in the process of water electrolysis; a gasifier for producing synthesis gas in a process of gasification of carbon-based fuel in the presence of a gasifying agent; and a methane synthesis reactor for producing methane in a process of synthesis of carbon oxide from the gasifier and hydrogen from a water electrolyser.

JP2018002751 describes a method of improving the efficiency of power generation, which involves gasifying woody biomass and generating power by burning the gas.

WO2018078661 describes a process for making pure hydrogen from a syngas.

WO2013064552 describes a process for the thermochemical conversion of a carbon-based feedstock to synthesis gas, comprising oxycombustion of the carbon-based feedstock to create a cogeneration of electricity and of heat; high-temperature electrolysis of water; and a reverse water gas shift reaction.

WO2008033812 describes a process for the conversion of a carbon containing moiety to liquid hydrocarbon fuel, comprising gasifying with a predetermined energy source at least a portion of the carbon containing moiety to produce a syngas stream containing carbon monoxide and hydrogen, at least a portion of the predetermined energy source being from a carbon-free energy source; and reacting the syngas stream to form liquid hydrocarbon fuel.

SUMMARY OF INVENTION

The object of the present invention is to provide a more environmentally friendly and economically optimal process for manufacturing a useful product such as synthetic fuel from waste materials and/or biomass materials and/or gaseous materials, in which the carbon intensity of the process is reduced in comparison to conventional processes for producing high molecular weight synthetic fuel. One way in which this is achieved in the present invention is with the use of renewable feedstock and energy sources that are implemented in an optimized way. The process according to the present invention therefore provides a process that increases the self-sufficiency of the overall plant facility, increases the overall efficiency of the process, and lowers the environmental impact of the process, when compared to conventional methods.

Additionally, the process according to the present invention provides an economically optimal process, thereby improving the profitability of the overall process when compared to conventional methods in the art. This is achieved, for example, when looking at the electricity usage for providing $H_2$ to the process. It is known that the price of electricity fluctuates throughout the day and the inventors have advantageously found that optimising the process according to the present invention and implementing advanced control mechanisms to optimise the process to control the fluctuating costs, can significantly improve operation and profitability. The process according to the present invention can therefore be adapted in response to different factors, which are often external, thereby improving the economics of the overall process.

A further object of the present invention is to provide an effective method for controlling the desired hydrogen to carbon monoxide ratio of the feed used to produce the useful product. The integration of several processes in the present invention offers a high degree of flexibility and gives the gasification zone the ability to handle a wide range of feedstock with fluctuating compositional characteristics, to achieve the desired $H_2$:CO molar ratio, which is superior to conventional methods in the art, particularly when utilising various different feedstocks.

According to a first aspect of the present invention, there is provided an integrated process for the production of a useful product comprising the steps of:
  feeding a gasification zone with an oxygen-containing feed and a first carbonaceous feedstock comprising waste materials and/or biomass,
  gasifying the first carbonaceous feedstock in the gasification zone to produce a first synthesis gas,
  optionally partially oxidising the first synthesis gas in a partial oxidation zone to generate partially oxidised synthesis gas,
  combining at least a portion of the first synthesis gas and/or the partially oxidised synthesis gas and at least a portion of electrolysis hydrogen obtained from an electrolyser in an amount to achieve a desired hydrogen to carbon monoxide molar ratio and to generate a blended synthesis gas; and
  subjecting at least a portion of the blended synthesis gas to a conversion or separation process effective to produce the product.

According to a second aspect of the present invention, there is provided an integrated process for the production of a useful liquid hydrocarbon product comprising the steps of:
  feeding a gasification zone with an oxygen-containing feed and a first carbonaceous feedstock comprising waste materials and/or biomass,
  gasifying the first carbonaceous feedstock in the gasification zone to produce a first synthesis gas,
  partially oxidising the first synthesis gas in a partial oxidation zone to generate partially oxidised synthesis gas,
  combining at least a portion of the first synthesis gas and/or the partially oxidised synthesis gas and at least a portion of electrolysis hydrogen obtained from an electrolyser in an amount to achieve a desired hydrogen to carbon monoxide molar ratio of from about 1.5:1 to about 2.5:1, which is higher than that of the first synthesis gas, and to generate a blended synthesis gas, wherein the electrolyser operates using green electricity; and
  subjecting at least a portion of the blended synthesis gas to a conversion process effective to produce the liquid hydrocarbon product.

The inventors of the present invention have surprisingly found that a process according to the invention provides an effective method for both reducing carbon intensity and controlling the $H_2$:CO molar ratio of synthesis gas in an optimized way, which is superior to conventional methods in the art. This is because the process of the present invention utilises any by-products produced throughout the process for recycled use in upstream and/or downstream stages and utilises renewable (i.e. green) feedstock. Therefore, the process according to the present invention is more environmentally friendly than conventional methods.

For example, electrolysis hydrogen and oxygen produced in the present invention is substantially pure and used in upstream and/or downstream processes. Therefore, in preferred embodiments, this may obviate the need for additional external feeds to supplement the synthesis gas and/or additional external processes to remove waste, that may otherwise be associated with conventional BTL and WTL processes. This has a significant impact on carbon intensity.

Preferably, at least a portion of the optionally partially oxidised synthesis gas and/or first synthesis gas generated downstream is decontaminated in a clean-up zone. This step will alleviate poisoning of any catalyst utilised in a subsequent conversion process.

The conversion process will typically result in a high molecular weight (e.g. liquid) hydrocarbon whereas a separation process may be used to produce hydrogen or carbon dioxide, for example.

The process of the present invention is configurable to control the molar $H_2$ to CO ratio of the blended synthesis gas to provide the desired molar $H_2$ to CO ratio by combining synthesis gas resulting from a waste and/or biomass derived synthesis gas and electrolysis hydrogen.

The blended synthesis gas may have a higher hydrogen to carbon monoxide molar ratio than the synthesis gas leaving the gasification zone and/or partial oxidation zone.

The molar $H_2$ to CO ratio may optionally be adjusted by at least one of green hydrogen; water gas shift reaction; reforming-derived synthesis gas, for example steam methane reforming or autothermal reforming; reverse water gas shift reaction. Thus, the configurability of the plant is such as to make it capable of controlling the molar $H_2$ to CO syngas ratio, even where a variety of different feedstocks with a wide variety of compositional characteristics may be used. This has the advantage that the process of producing useful products, such as transportation fuel, is optimised and reduces the complexity of the process in comparison with conventional processes of the type.

Accordingly, by "different in its compositional characteristics" we mean that the compositional variation between the carbonaceous feedstocks may be considerable over time—as between, for example, different types of commercial or industrial waste or between different types of biomass, or even changing from biomass to commercial or industrial waste or a combination of both feedstocks—with varying ratio of the two components.

The process of the invention is therefore concerned with the practicality of generating consistently and efficiently useful products from variable carbonaceous feedstocks and energy sources, preferably where the feedstocks are renewable.

For example, non-recyclable waste is conventionally sent to landfill or incineration and woody biomass is conventionally left on a forest floor and/or may contribute to forest fires. The process according to the present invention advantageously provides a lower emissions route to process waste than incineration or landfill. Instead of being burnt, the carbon waste may be converted into a useful product such as sustainable fuel for use in aircraft or vehicles.

For example, when renewable electricity is used to power the electrolyser and electrolysis reaction, the resulting products are considered carbon-neutral and do not contribute to harmful emissions, thereby having a significant impact on carbon intensity and greenhouse gas emissions.

For example, when renewable natural gas is used as the feedstock for the reforming process the biogenic content of the useful products (i.e. fuel) is preserved, thereby having a significant impact on carbon intensity and greenhouse gas emissions.

Preferably, the process of the present invention is a continuous process wherein carbonaceous feedstock, of whatever nature provided it is derived from waste materials and/or biomass, is continuously fed to a gasification zone for gasifying the carbonaceous feedstock.

The gasification zone may be continuously fed with an oxygen-containing feed comprising oxygen generated from a renewable source, such as electrolysis.

Preferably, the majority, if not all, of the oxygen-containing feed fed to the gasification zone is from a renewable source. If the demand cannot be met solely with an oxygen-containing feed from a renewable source, supplementary oxygen from a traditional oxygen unit, such as an air separation unit, may be used.

In preferred embodiments, the oxygen demand of the gasification zone may be achieved without the requirement of an air separation unit.

Preferably, an electricity source, of whatever nature provided it is considered "green" or renewable, is continuously fed, either simultaneously or separately to an electrolyser for the electrolysis of water.

It is to be understood that the terms "renewable", "green" and/or "clean" when used to describe feedstock and/or energy sources are construed to mean that they are from a natural resource or source of energy that is not depleted by use. They are produced with little-to-no environmental impact and do not contribute greenhouse gases into the air the way fossil fuels do.

Optionally, a carbonaceous feedstock, of whatever nature provided it is gaseous material, may be continuously fed, either simultaneously or separately to a reforming unit for gasifying the carbonaceous feedstock.

The carbonaceous feedstock used as a feed for the reforming unit may optionally be compositionally different to the carbonaceous feedstock feed used for the gasification zone. The term "carbonaceous feedstock" should not be taken as limiting and the skilled person would understand the differences to the carbonaceous feedstock fed the gasification zone in comparison to the carbonaceous feedstock fed to the reforming unit.

At least a portion of the synthesis gas (for example, blended synthesis gas) is fed into a synthesis unit. Non-limiting examples of suitable syntheses include Fischer-Tropsch, ammonia synthesis, methanol synthesis, alcohol synthesis or hydrogen production.

The useful product may be produced by subjecting at least part of the blended synthesis gas to a Fischer-Tropsch synthesis or ammonia synthesis or methanol synthesis.

Synthesis reactions require specific hydrogen to carbon monoxide ratio in feed gas ("desired ratio") for optimum performance to meet process requirements, maximise conversion and product yield.

As a non-limiting example, it is generally needed to increase the hydrogen to carbon monoxide ratio of the synthesis gas generated from waste-derived gasification when wanting to supply clean synthesis gas to a Fischer-Tropsch reactor. As a result, at least part of the synthesis gas from, for example, a clean-up zone (ie. clean synthesis gas) may be combined with at least a portion of the electrolysis hydrogen from the electrolyser and/or synthesis gas from the reforming unit and/or at least a portion of green hydrogen to adjust the hydrogen to carbon monoxide ratio to the desired range.

As a non-limiting example, the molar ratio of $H_2$ to CO in the synthesis gas leaving the reforming unit, when the reforming unit is a steam methane reforming unit, is desirably in the range from about 2:1 to about 7:1, or preferably from about 2.5:1 to about 6.5:1, or more preferably from about 3:1 to about 6:1. The molar ratio of $H_2$ to CO in the raw synthesis gas leaving the reforming unit is referred to herein as "hydrogen rich gas".

As a further non-limiting example, the molar ratio of $H_2$ to CO in the synthesis gas leaving the reforming unit, when the reforming unit is a autothermal reforming unit, is desirably in the range from about 1.5:1 to about 4.0:1, or preferably from about 2.0:1 to about 3.0:1, or more preferably from about 2.0:1 to about 2.5:1. The molar ratio of $H_2$ to CO in the raw synthesis gas leaving the reforming unit is most preferably about 2.4:1. The molar ratio of $H_2$ to CO in the raw synthesis gas leaving the reforming unit may also be referred to as "hydrogen rich gas". The skilled person would understand the difference in the $H_2$:CO molar ratio of synthesis gas leaving a steam methane reforming unit when compared to an autothermal reforming unit.

As a non-limiting example, the Fischer-Tropsch synthesis feed (i.e. blended synthesis gas) may have a hydrogen to carbon monoxide ratio of about 2. As a non-limiting example, the Fischer-Tropsch synthesis $H_2$:CO ratio may from about 1.5:1 to about 2.5:1, or preferably from about 1.7:1 to about 2.2:1, or more preferably from about 1.95:1 to about 2.05:1, typically about 2.

It has been found that by combining at least a portion of the waste derived synthesis gas (i.e. low $H_2$ to CO molar ratio) with at least a portion of pure hydrogen (i.e. electrolysis hydrogen and/or green hydrogen) and/or a "hydrogen rich" synthesis gas (i.e. reforming-derived synthesis gas), a blended synthesis gas is produced with a desired $H_2$ to CO molar ratio for the required synthesis, for example Fischer-Tropsch synthesis.

Preferably, the adjusting of the $H_2$ to CO molar ratio of the waste derived synthesis gas is achieved by the combination of feedstocks which are from renewable sources. This has a significant impact on both the carbon intensity and economics of the process.

For example, the different feeds utilised by the process according to the present invention have differing costs of production, for example, the price of waste composition may vary significantly depending on season and is source dependent.

The inventors of the present invention have advantageously found that a process according to the invention is able to control the ratios of the different feedstocks used (taking into account the price fluctuations), whilst still maintaining the desired $H_2$ to CO molar ratio composition, thereby significantly optimising the process and lowering the facility operating costs.

Additionally, as the pricing is cyclical, the process according to the present invention uses advanced control mechanisms that can significantly improve operation and profitability.

The useful product may optionally be produced by subjecting at least part of the synthesis gas to a Fischer-Tropsch synthesis.

According to the embodiment relating to Fischer-Tropsch synthesis, the optionally blended synthesis gas may be fed into a FT reactor.

The synthesis unit may be a FT unit comprising FT reactors. The FT reactors may comprise microchannels. Filters may be used to remove any particulates.

The FT reactor may convert at least part of the carbon monoxide and hydrogen of the optionally adjusted fine synthesis gas into mainly linear hydrocarbons.

The blended synthesis gas may be converted by Fischer-Tropsch synthesis into liquid hydrocarbons.

The conversion of synthesis gas into liquid hydrocarbons may optionally be in the presence of a catalyst. The chain length distribution will be dependent on the properties of the catalyst used and the operating conditions.

Fischer-Tropsch reactions are exothermic and release heat that must be removed to keep the temperature of the reaction approximately constant. Localised high temperatures in the catalyst bed have been found to adversely affect the FT product mix, yield and potentially reduce catalyst life. Therefore, it is desirable to keep the temperature constant.

The temperature may be controlled by varying pressure of a steam drum associated with the FT reactor used in conjunction with circulating cooling water.

The operating temperature for the FT synthesis may be between about 125 and 350° C., between about 150 and 300° C., between about 170 and 250° C., between about 180 and 240° C. Preferably, the operating temperature is between about 180 and 240° C. for a low temperature FT technology.

The catalyst may be a metal or compounded metal catalyst with a support. In one embodiment, the metal is cobalt. The support may be made from silica and/or titania.

The products that may be obtained in the FT synthesis, for example, said hydrocarbons, may include heavy FT liquid (HFTL), light FT liquid (LFTL), FT process water, naphtha, and tail gas comprising of inerts as well as uncondensed light hydrocarbons, typically C1 to C4. A part of the tail gas comprising of light hydrocarbons, C1 to C4 range, may be recycled back to the partial oxidation zone or sent to a fuel gas system.

It is desirable to upgrade the liquid hydrocarbons into a useful product.

The liquid hydrocarbons may be upgraded to make a useful product. At least part of the liquid hydrocarbons may be upgraded by at least one of hydroprocessing, hydrotreating, product fractionation, hydrocracking and/or hydroisomerisation for example.

The FT liquid upgrading unit may for example produce high quality naphtha and Synthetic Paraffinic Kerosene (SPK). Other upgraded products may for example include gasoline, diesel and waxes. The unit may for example be configured as a recycle hydrocracker.

The useful product may for example be sustainable liquid transportation fuel or a gasoline blendstock. SPK and/or diesel and/or naphtha may be combined with another fuel component to make a transportation fuel. The transportation fuel or gasoline blendstock may for example be used for aviation and/or vehicles. The sustainable liquid transportation fuel may for example comprise high quality diesel and/or SPK. The gasoline blendstock may for example comprise naphtha.

As a result of the supply of high purity electrolysis hydrogen provided to combine with waste and/or biomass derived synthesis gas, the desired molar ratio may be achieved without the requirement of a water gas shift reaction, as is conventionally used.

Accordingly, in one embodiment, the process according to the present invention does not include a water gas shift reaction.

However, if renewable natural gas and/or electrolysis hydrogen supply is limited as the feedstock, some water gas shift capacity may be included in order to achieve the desired molar ratio of $H_2$:CO.

The products formed by a process according to the present invention may constitute cleaner versions of fuels formed by conventional processes.

Technologies that may be utilised in accordance with the present invention to produce the electrolysis hydrogen and oxygen may for example comprise an electrolyser which may undergo at least one of alkaline water electrolysis, solid polymer water electrolysis, high temperature solid oxide water electrolysis.

The process of the invention may obtain electrolysis hydrogen and electrolysis oxygen through the electrolysis of water in an electrolyser. Advantageously, water electrolysis is an efficient and clean hydrogen production technology.

The electrolyser may be operated using an external source of electricity. Preferably, the source of electricity is from a renewable (green) source. The electrolyser may operate using green technology, for example, low carbon power.

The electrolyser may operate using low carbon electricity, also termed green electricity.

Low carbon power is a result of processes or technologies that produce power with substantially lower amounts of carbon dioxide emissions than is emitted from conventional fossil fuel power generation. For example, low carbon power may include power generation from wind power, solar power, hydroelectric power, geothermal power, and/or nuclear power.

Typically, the power consumption of an electrolyser is high and can be costly, therefore it is important to utilise "clean" energy and to minimise, or preferably obviate, importation of external "dirty" energy, which has a significant impact on the carbon intensity of the overall process.

Further, it is important to utilise all by-products generated within the plant facility to optimize the use of the integrated electrolyser and reduce any waste products, thereby impacting the carbon intensity of the overall process.

The source of green electricity supplied to the electrolyser may for example be wind power, solar energy, or a renewable reformer fuel such as biogas, ethanol or renewable natural gas, such as bio-diesel.

Advantageously, the use of a renewable electricity source for electrolysis will make the generation of electrolysis oxygen and hydrogen virtually carbon-neutral and thus will not contribute to the overall carbon intensity of the process. The process of the invention therefore provides a lower emissions route to the production of a useful product, particularly when compared to processes that utilise hydrogen generated from fossil hydrocarbons.

It is therefore desirable to use renewable electricity sources where possible thereby reducing the carbon dioxide and greenhouse gas levels and thus reducing carbon intensity of the overall process.

The process according to the present invention therefore does not require the importation of hydrogen generated from fossil fuels. In an embodiment where electrolysis hydrogen is not sufficient, hydrogen may be generated from a different renewable source.

The process of the invention is therefore configurable to control the carbon intensity of the process responsive to other, often external, factors. For example, the facility benefits from the readily available clean, green power, such as may be generated by a wind turbine on a windy day for example, then it is desirable to maximise product make on plant, as the power required to make the product is green. The process according to the invention therefore obviates the requirement for importation of "dirty" power from the grid.

Advantageously, the process according to the present invention utilises standard measuring and sampling equipment, as well as macroeconomic data, to optimise feed ratios based on external factors, to provide a more cost-effective and environmentally friendly route to the manufacture of a useful product.

The feedstocks fed into the process of the present invention therefore may be adjusted responsive to external factors.

The major products leaving the electrolyser are oxygen and hydrogen, referred to herein as "electrolysis oxygen" and "electrolysis hydrogen".

Advantageously, when clean power is used to supply the energy for electrolysis, the resulting by-products are also considered "green" and therefore do not contribute to the carbon intensity value.

The electrolysis oxygen and/or electrolysis hydrogen may be substantially pure. By substantially pure we mean at least about 98% pure, at least about 99% pure, at least about 99.5% pure, about 99.8% pure.

The electrolysis hydrogen and electrolysis oxygen may be used in upstream and/or downstream processes. Advantageously, using both the products of the electrolysis reaction within the plant facility reduces, and in preferable embodiments obviates, the requirement to import hydrogen and oxygen from other non-renewable and/or external sources. Additionally, the use of both major products within the plant facility ensures that there are no waste products, or extra processes required to remove components from the plant. Therefore, providing both electrolysis hydrogen and oxygen to existing processes in the plant facility can advantageously reduce the carbon intensity associated with the plant.

For example, electrolysis oxygen may be used in upstream processes, such as supplying a feed into the gasification zone.

For example, electrolysis hydrogen may be combined with synthesis gas (i.e. raw synthesis gas) prior to entering the reaction unit (i.e. FT reaction unit), in an amount to achieve the desired ratio.

This has the advantage that the process of producing useful products, such as transportation fuels, is optimised and reduces the complexity of the process in comparison with conventional processes of the type.

The inventors have found that the supply of pure hydrogen may obviate or reduce the need for additional downstream processes, such as a water gas shift reaction, to obtain the desired molar ratio, as is conventionally used.

Accordingly, in one embodiment, the process according to the present invention does not include a water gas shift reaction.

Additionally, or alternatively, electrolysis hydrogen may be used as a feed to a reverse water gas shift (RWGS) reactor.

When hydrogen is used to adjust the $H_2$:CO molar ratio of synthesis gas, the hydrogen will preferably be from a green or renewable source. Thus, if the supply of electrolysis hydrogen does not satisfy the demand of the process and/or achieve the desired $H_2$:CO molar ratio, green hydrogen from a separate feed may optionally be additionally supplied.

Accordingly, in some embodiments the process may comprise a green hydrogen feed. The green hydrogen feed may be separate to the electrolysis hydrogen feed.

The green hydrogen gas may therefore be combined with at least one of electrolysis hydrogen and/or partially oxidised synthesis gas and/or clean synthesis gas and/or second synthesis gas. The use of green hydrogen therefore does not negatively impact the carbon intensity of the overall process.

Electrolysis oxygen may be used as a feed to the gasification zone. The electrolysis oxygen may be used to supplement the quantity of oxygen otherwise supplied by other means to the gasification zone, for example via an air separation unit (ASU). In preferred embodiments, the oxygen demand of the gasification zone may be achieved without the requirement of an air separation unit.

However, if electrolysis oxygen supply is limited or does not meet the demand, some air separation unit capacity may be included.

Accordingly, in one embodiment, the process according to the present invention does not include an air separation unit.

Advantageously, the integration of feeding the electrolysis oxygen into the gasification zone and combining electrolysis hydrogen with synthesis gas, maximizes the utility of the electrolyser and in some embodiments, obviates the need of a separate air separation unit and/or water gas shift reaction, thereby reducing costs and increasing simplicity of the plant. Thus, the complexity of the process according to the present invention is reduced when compared to conventional processes in the art.

The process according to the invention therefore provides a process that integrates a gasification process with an electrolysis process which has the potential to overcome environmental issues associated with oxygen and hydrogen which would otherwise be supplied to the plant by alternative non-renewable sources and/or methods.

The process according to the present invention may include producing a second synthesis gas to achieve the desired $H_2$:CO molar ratio.

Technologies that may be utilised in accordance with the present invention to produce a second synthesis gas may include for example, steam methane reforming (SMR) and autothermal reforming (ATR).

Other suitable reforming methods may optionally include carbon dioxide reforming and partial oxidation.

In some embodiments, the plant facility will operate effectively and obtain the desired $H_2$:CO ratio without the requirement of a reforming unit.

However, a reforming process (with an integration unit) may be integrated into the process if required to obtain the desired $H_2$:CO molar ratio. Additionally, a reforming process may be integrated to increase the supply of synthesis gas, in order to meet demand. Preferably, the feedstock fed to the reforming unit is renewable.

In some embodiments, the process according to the invention may be integrated with a reforming process.

Steam methane reforming is a non-oxidative process that converts the feedstock into hydrogen and carbon monoxide by the following reaction:

$$CH_4 + H_2O \rightarrow CO + 3H_2$$

The major products leaving the SMR unit are typically steam and raw synthesis gas. Other by products may also be formed such as carbon dioxide and solid carbon for example.

The molar ratio of $H_2$ to CO in the raw synthesis gas leaving the reforming unit, when the reforming unit is an SMR unit, is desirably in the range from about 2:1 to about 7:1, or preferably from about 2.5:1 to about 6.5:1, or more preferably from about 3:1 to about 6:1.

The reforming operating temperature may vary depending on the compositional characteristics of the carbonaceous feedstock and the reforming reaction that is employed.

The operating temperature of the SMR unit is preferably at least about 500° C., more preferably above 600° C., 700° C. or 800° C. The operating temperature of the SMR unit may for example be between about 500° C. and 1200° C., preferably between about 600° C. and 1100° C., or more preferably between about 700° C. and 1000° C.

It has been found that a high temperature is required to ensure a high conversion of methane to synthesis gas. It is desirable to keep the temperature constant to prolong catalyst life and improve product yield.

It has advantageously been found that if the facility is short of steam, it is possible to conduct "duct-firing" in the reforming unit in order to raise additional saturated and/or superheated steam without having to install a standalone boiler, which is desirable.

Typically, the furnace used to heat the reaction may be fired with waste off-gas from the plant facilities and may be supplemented with pipeline natural gas. However, if the carbon intensity target is proving difficult to meet, it may be possible to fire the reformer unit with renewable natural gas and offset any deficit in the carbon intensity score.

It is desirable to have a pressure within the reforming unit that will maximise methane conversion and minimise residual methane.

The reforming reaction may optionally be in the presence of a catalyst. The catalyst may be a metal or compounded meal catalyst with a support. The catalyst may be a heterogeneous catalyst. In one embodiment, the catalyst is nickel-based. The support may optionally be made from alumina.

The reactor in the reforming unit, for example an SMR unit, may be composed of tubes filled with solid catalyst. The tubes may be placed in a furnace that is heated to the desired temperature for the reforming reaction, for example with a gas burner.

In another embodiment the second synthesis gas may be produced by autothermal reforming. Autothermal reforming uses oxygen and carbon dioxide or oxygen and steam in a reaction with methane to form carbon monoxide and hydrogen. The autothermal reaction using oxygen and carbon dioxide can be described by the following reaction:

$$2CH_4 + O_2 + CO_2 \rightarrow 3H_2 + 3CO + H_2O$$

The autothermal reaction using oxygen and steam proceeds by the following reaction:

$$4CH_4 + O_2 + 2H_2 \rightarrow 10H_2 + 4CO$$

The molar ratio of $H_2$ to CO in the raw synthesis gas may be lower when leaving an autothermal reforming unit when compared with a steam methane reforming unit. The molar ratio of $H_2$ to CO in the raw synthesis gas will be greater when leaving an autothermal reforming unit when compared with the waste-derived synthesis gas.

For example, the molar ratio of $H_2$ to CO in the raw synthesis gas leaving the reforming unit, when the reforming unit is an ATR unit, is desirably in the range from about 1.5:1 to about 4.0:1, or preferably from about 2.0:1 to about 3.0:1, or more preferably from about 2.0:1 to about 2.5:1. The molar ratio of $H_2$ to CO in the raw synthesis gas leaving the reforming unit is most preferably about 2.4:1.

The amount of synthesis gas from the reforming unit combined with a first synthesis gas (for example waste and/or biomass derived synthesis gas) may be in an amount to achieve the desired hydrogen to carbon molar ratio. For example, a greater amount of synthesis gas from a reforming unit may be combined with a waste derived synthesis gas to meet the desired molar ratio when the reforming unit is an ATR unit when compared to an SMR unit.

The synthesis gas leaving the reforming unit may be combined with at least one other feed to meet the desired molar ratio. For example, the second synthesis gas may be combined with at least a portion of the first synthesis gas and/or partially oxidised synthesis gas and/or at least a portion of the clean synthesis gas and/or at least a portion of the electrolysis hydrogen in an amount to achieve the desired hydrogen to carbon monoxide molar ratio.

Accordingly, the blended synthesis gas may comprise the second synthesis gas and/or partially oxidised synthesis gas and/or clean synthesis gas and/or electrolysis hydrogen in an amount to achieve the desired hydrogen to carbon monoxide molar ratio.

The blended synthesis gas feed desirably comprises $H_2$ and CO in a molar ratio in the range from about 1.5:1 to about 2.5:1, or preferably from about 1.7:1 to about 2.2:1, or more preferably from about 1.95:1 to about 2.05:1. The desired $H_2$ to CO molar ratio of the blended synthesis gas is most preferably about 2.

The carbonaceous feedstock used as feed for the reforming unit may optionally be compositionally different to the carbonaceous feedstock feed used for the gasification zone.

The carbonaceous feedstock may comprise biogenic carbon. The carbonaceous feedstock may comprise renewable waste.

In some embodiments, the carbonaceous feedstock may comprise flare gas.

The carbonaceous feedstock being fed into the reforming unit may be a gas.

The carbonaceous feedstock being fed into the reforming unit may for example comprise at least one of natural gas (e.g. methane), renewable natural gas, biogas, low-carbon methanol, and/or low-carbon ethanol. Preferably, the feedstock comprises a renewable natural gas.

Advantageously, renewable natural gases are a carbon neutral fuel source because they come from organic sources that once absorbed carbon dioxide from the atmosphere during photosynthesis. It is therefore desirable to use renewable natural gas where possible thereby reducing the carbon dioxide and greenhouse gas levels and thus reducing carbon intensity of the overall process.

The use of a renewable natural gas as the feedstock has been found to preserve the biogenic content of the useful product, such as transportation fuel. Therefore, where renewable natural gas is used as the feedstock to the reforming unit, the biogenic content of the resulting useful product will be greater when compared to the biogenic content of a waste-derived product only.

As a result, the resulting transportation fuel, for example, may be considered to be a partially renewable fuel, a fuel having reduced carbon intensity and/or a fuel having renewable content.

The above preferred embodiments of the present invention therefore provide a more environmentally friendly process to manufacturing a useful product when compared to conventional process in the art.

Biogas may optionally be obtained from biomass, residues or wastes by anaerobic digestion. Biogas may be optionally upgraded and/or purified to become renewable natural gas.

Prior to the carbonaceous feedstock entering the reforming unit, the feedstock may optionally be purified. For example, sulphur may be removed from the feedstock prior to entering the reforming unit as sulphur, if present, may otherwise poison the catalyst. It is therefore desirable to remove sulphur upstream of the reformer unit to promote prolonging of the catalyst life and alleviate poisoning of the catalyst downstream.

Sulphur may be removed by any suitable method known by the skilled person in the art. For example, removal of hydrogen sulphide may be achieved by adsorption on an active carbon-fixed bed, which may for example be a zinc oxide bed and/or iron oxides which have a high affinity for such pollutants, for example. Adsorbents used for sulphur removal may be, for example, iron oxide, zinc oxide and/or mixed copper-zinc oxides. The resulting gas is referred to herein as "partially purified". Other components such as water, hydrocarbons, chloride, and/or any compounds that may prove detrimental to a downstream catalyst may additionally be optionally removed from the feedstock prior to reforming.

Unless the context dictates otherwise, the terms "raw synthesis gas", "clean synthesis gas", "blended synthesis gas", "partially oxidised synthesis gas" and any other phrase containing the term "synthesis gas" are to be construed to mean a gas primarily comprising hydrogen and carbon monoxide. Other components such as carbon dioxide, nitrogen, argon, water, methane, tars, acid gases, higher molecular weight hydrocarbons, oils, tars, volatile metals, char, phosphorus, halides and ash may also be present. The concentration of contaminants and impurities present will be dependent on the stage of the process and carbonaceous feedstock source. It is to be understood that carbonaceous material, for example, $CH_4$ and inert gas such as $N_2$ present in the raw synthesis gas generated is expected to be carrier forth through each of the subsequent steps and may not be explicitly mentioned.

The use of such terms to describe synthesis gas should not be taken as limiting. The skilled person would understand that each of the terms is construed to mean a gas primarily comprising hydrogen and carbon monoxide.

The carbonaceous feedstock for gasification may for example comprise at least one of woody biomass, municipal solid waste and/or commercial and industrial waste. The carbonaceous feedstock will typically have fluctuating compositional characteristics that are dependent on the source and chemistry of the feedstock used.

The carbonaceous feedstock may for example be in the form of relatively large pieces. The carbonaceous feedstock may optionally be processed to remove oversized items, recyclates, highly halogenous plastics such as PVC, metals and inert items. These items cannot be converted into synthesis gas and/or are likely to a significant contaminant load (for example, the case of highly halogenous plastics); therefore, it is preferable to remove said items prior to gasification. These items may optionally be recycled.

The carbonaceous feedstock may optionally be reduced to a size suitable for gasification. For example, the carbonaceous feedstock may be comminuted, shredded or chipped prior to gasification.

In some embodiments, the carbonaceous material feedstock is biomass, for example woody biomass feedstock. Examples of suitable woody feedstock may include tree length round wood, pulpwood thinnings, whole tree, limbs, branches, tops and/or waste wood.

In another embodiment, the carbonaceous feedstock is waste material, for example municipal solid waste and/or commercial and industrial waste.

The carbonaceous feedstock may also be Solid Recovered Fuel (SRF) which is a waste product of relatively high calorific value typically derived from paper, card, wood, textiles and plastics.

The carbonaceous feedstock may typically comprise moisture. Preferably in that case, the carbonaceous feedstock is dried to at least some extent prior to gasification.

The carbonaceous feedstock may optionally be conveyed to a dryer to reduce the moisture content to a suitable level. The moisture content may for example be reduced to less than about 20%, preferably less than about 15% or most preferably less than about 10% by weight. Preferably, the carbonaceous feedstock supplied to the gasification zone has a moisture content of at most 10% by weight; depending on the requirements of the gasification technology deployed.

When waste material is used as the carbonaceous feedstock source, the feedstock may not need drying prior to entering the gasification zone. Waste material in this case may be fed directly into the gasifier, optionally after suitable pre-treatment to remove undesirable components and comminute the feedstock to a size suitable for feedstock handling.

The process of the invention obtains raw synthesis gas through gasifying the carbonaceous feedstock in a gasification zone. Gasification may occur in the presence of steam and an oxygen-containing feed. The oxygen-containing feed may comprise electrolysis oxygen obtained from an electrolyser. The electrolyser may be located upstream of the gasification zone.

Electrolysis oxygen may be used to supplement the quantity of oxygen fed to the gasification zone that may otherwise be supplied by a different means, such as an air separation unit (ASU), for example. In some embodiments, the use of electrolysis oxygen from an electrolyser may obviate the need of an air separation unit and its associated costly plant.

Accordingly, in one embodiment gasification of the carbonaceous feedstock may be achieved without the requirement of an air separation unit. However, if oxygen supply is limited, some air separation unit capacity may be included in order to satisfy the oxygen demand.

The oxygen-containing feed may comprise other oxygenated gaseous components. The oxygen-containing feed may refer to all gases being fed to the gasifier, whether the gases were combined upstream of the gasification zone or within the gasification zone.

The quantity of electrolysis oxygen supplied to the gasification zone may be dependent on the compositional characteristics of the feedstock fed into the gasification zone and the volume of feedstock required to be gasified. The electrolysis oxygen may be fed to the gasification zone in an amount to satisfy the oxygen demand of the gasifier. Advantageously, the gasification zone according to the present invention has the ability to handle a wide range of different feedstocks.

The gasification zone may comprise a singular train, dual trains or multiple trains. Preferably, the gasification zone comprises more than one train to minimize the impact of interruptions on the plant availability.

Three primary types of commercially available gasifiers are of fixed/moving bed, entrained flow, or fluidized bed type. The gasification zone may for example be an indirect gasification zone in which feedstock and steam are supplied to a gasification vessel which is indirectly heated.

In another embodiment, the gasification zone may be a direct gasification zone in which feedstock, steam and an oxygen-containing gas are supplied to the gasification vessel and directly combusted to provide the necessary heat for gasification. Also known in the art and suitable for use in the process of the present invention are hybrid gasifiers, and gasifiers incorporating partial oxidation units. In that case it will be understood that in the process of the invention the gasification zone and the partial oxidation zone may be separate zones of a single vessel.

In one embodiment, the gasification zone comprises primarily an indirectly heated deep fluidized bed operating in the dry ash rejection mode and a secondary gasifier, for maximal conversion of the carbonaceous material. In another embodiment, the gasification zone may comprise only a primary indirectly heated fluidized bed.

The fluidised bed operating temperature may vary depending on the compositional characteristics of the carbonaceous feedstock. The fluidised bed operating temperature may be between about 400 and 1000° C., preferably between about 500 and 900° C., or more preferably between about 600 to 800° C.

Such temperature ranges of the fluidised bed have been found to avoid any constituent ash from softening and forming clinkers with the bed material.

The fluidized bed reactor may optionally be preloaded with a quantity of inert bed media such as silica sand or alumina for example.

The inert bed media may optionally be fluidized with superheated steam and oxygen.

The superheated steam and oxygen may optionally be introduced through separate pipe nozzles.

During gasification, the fluidized bed may optionally undergo drying (or dehydration), devolatilization (or pyrolysis) and gasification.

Some combustion, water gas shift and methanation reactions may also occur during gasification.

It is desirable to have a pressure within the gasification zone that minimises the need of compression in downstream processes. It is therefore preferable for the gasification zone to have a pressure of at least about 3.5 bar if not higher, for example about 4 bar or more. Gasification zones operating at even much higher pressures such as 10 bar or more are known in the art. Similarly, gasification zones operating at lower pressures, for example about 1.5 bar or less are also known in the art.

The raw synthesis gas leaving the gasification zone may optionally have an exit temperature of at least about 600° C., preferably of at least about 700° C., or more preferably of at least about 800° C. Desirably, the raw synthesis gas leaving the gasification zone has an exit temperature of from about 700° C. to about 750° C.

The major products leaving the gasification zone are typically steam and raw synthesis gas comprised of hydrogen and carbon monoxide (CO) (the essential components of synthesis gas), carbon dioxide ($CO_2$), methane, and small amounts of nitrogen and argon. There may be additional tars such as benzene, toluene, ethyl benzene and xylene, higher hydrocarbons, waxes, oils, ash, soot, bed media components and other impurities present.

In order to obtain high-quality gas that is required for its use as a feedstock in downstream processes such as synthesis, it is highly desirable, at least if the downstream process involves a catalyst, to remove the impurities. Non-limiting examples include Fischer-Tropsch (FT) synthesis, ammonia synthesis, methanol synthesis, or separation as a hydrogen product.

Carbon dioxide, sulphur, slag and other by-products and impurities of gasification may be amenable to capture, collection and reuse.

Cyclones may be used to remove undesirable solid materials from the raw synthesis gas.

A tramp discharge system may optionally be used to remove heavier contaminants from the bed material in operation of the gasification process.

The hydrogen to carbon monoxide ratio in the feed and/or term "feed ratio" is to be construed as the volume of hydrogen per volume of carbon monoxide in the relevant feed stream.

The presence of impurities can influence the processing conditions of downstream processes and further steps may be required to remove any impurities present. It is desirable to control the hydrogen to carbon monoxide ratio in the raw synthesis gas to improve the overall performance, product yield and optimisation when compared to conventional methods.

Depending on the source of carbonaceous feedstock and the gasification technology, the raw synthesis gas may for example comprise between about 3 and 40% carbon dioxide, in addition to other impurities and contaminants.

The raw synthesis gas leaving the gasification zone may typically comprise a varying sulphur concentration depending on the source of the feedstock being gasified, typically in the hundreds of ppm.

The concentration of sulphur in the raw synthesis gas will influence the process conditions that are employed downstream.

At least part of the raw synthesis from the gasification zone is recovered and at least part of the recovered raw synthesis gas may be supplied to a partial oxidation zone (POx zone). The raw synthesis gas in the partial oxidation zone will undergo partial oxidation reactions. The resulting gas leaving the POx zone is referred herein as "partially oxidised synthesis gas".

It has been found that by employing a POx zone the carbon intensity can be reduced sufficiently to allow the rest of the plant facility to be simplified, thereby benefitting the economics of the process.

Furthermore, the inclusion of a partial oxidation zone offers flexibility and gives the gasification zone the ability to the handle of a wide range of feedstock with fluctuating compositional characteristics.

It has unexpectedly been found that a partial oxidation zone is able to remove hydrocarbonaceous materials such as methane, benzene, toluene, ethyl benzene, xylene, higher hydrocarbons and other tars to an extent sufficient to allow the straightforward optional recovery downstream of carbon dioxide in a form sufficiently pure for sequestration or other use, thereby reducing the carbon intensity of the process compared with conventional WTL and BTL processes.

Conventional partial oxidation zones in the art are typically catalytic or non-catalytic (thermal).

The partial oxidation zone may optionally partially combust tail gas from a downstream synthesis unit and/or natural gas with preheated oxygen and/or steam.

The partial oxidation zone may optionally comprise a burner utilising a stream of hot oxygen.

Typically, at least some of any tars, naphthalene, higher hydrocarbons and methane present in the partial oxidation zone are converted into carbon oxides, hydrogen and water.

The partial oxidation zone may operate at a temperature of least about 1100° C., at least about 1200° C. or at least about 1300° C. for example. Preferably, the partial oxidation zone operating temperature is at least about 1300° C., more preferably in the range of from about 1200° C. to about 1350° C.

The synthesis gas fed into the partial oxidation zone is subjected to partial oxidation to produce partially oxidised synthesis gas and steam may be generated by heat exchange with the gas heated in the partially oxidation zone.

The partially oxidised synthesis gas leaving the partial oxidation zone will be hot and may optionally be cooled by generating steam. Generation of superheated steam and/or saturated high-pressure steam is desirable to improve process efficiency and reduce carbon intensity.

The partially oxidised synthesis gas optionally generates high-pressure steam in a Heat Recovery Steam Generation (HRSG) unit when exiting the POx zone. The high-pressure steam has a high energy efficiency and may optionally be recovered and recycled for use in upstream and/or downstream process which allows energy to be recovered.

Recovery of heat from POx zone may typically be radiant and convective. A simple quench approach may also be used if the carbon intensity score allows.

The advantage of this radiant and convective heat recovery mode is the ability to have High Pressure (HP) steam (generated in a HRSG unit) available for use in the facility.

While water quench is also an acceptable (and lower cost) heat recovery option, it negatively impacts the carbon intensity of the facility owing to the need to generate HP steam for users in the plant such as the gasification unit, through use of additional natural gas and/or power.

The solids may optionally be removed as a slag from the POx zone.

The raw synthesis gas from the POx zone may optionally undergo at least one of gas clean up, compression and/or sulphur removal.

The synthesis gas may optionally remove ammoniacal, sulphurous and carbon dioxide (and other acid gases) impurities, preferably sequentially, in the clean-up zone.

The overall process according to the invention may optionally include additional stages. Therefore, the synthesis gas cleaned by sequentially removing ammoniacal, sulphurous and carbon dioxide impurities may be, for example, raw synthesis gas and/or partially oxidised synthesis gas.

The cooled partially oxidised synthesis gas may optionally be passed through a venturi scrubber to remove any water and particulates such as ash and soot. A caustic wash may for example be additionally used to remove any other impurities such as ammonia, halides, nitrous oxides and remaining particulates.

The partial oxidation zone may optionally operate at a pressure slightly or somewhat lower than that of the gasification zone (to avoid any intermediate compression requirements). The partial oxidation zone may operate at a pressure of between about 2 and 3 bar for a gasification process that operates around 3.5 bar, for example.

In another embodiment, the first synthesis gas may be subjected to partial oxidation and natural gas, preferably renewal natural gas, and may be combusted in the partial oxidation zone.

Optionally, a water gas shift reaction unit may be located downstream of the POx zone to increase the hydrogen content of the synthesis gas, processing for example the raw synthesis gas and/or partially oxidised raw synthesis gas.

The term "water gas shift reaction" or "WGS" is to be construed as a thermochemical process comprising converting carbon monoxide and water into hydrogen and carbon dioxide.

It has been found that the desired hydrogen to carbon monoxide molar ratio can be achieved without the requirement of a water gas shift reaction, as is conventionally used.

In preferred embodiments, the process of the present invention may not include a separate water gas shift reaction.

At least a portion of the optionally partially oxidised synthesis gas may be fed to a clean-up zone to remove contaminants to form "clean synthesis gas".

The clean-up process may, for example, be a physical absorption process, for example a solvent-based process. Suitable processes include low steam processes such as the Rectisol™ or Selexol™ processes, for example.

In one embodiment, the physical absorption unit may be configured to operate a dual stage process with two separate absorber columns that contact the synthesis gas stream with methanol comprising a common methanol regeneration system. The first absorber column may selectively remove sulphur and may use a $CO_2$ saturated solvent to minimise $CO_2$ absorption in the sulphur removal column. The second absorber column may recover $CO_2$.

This technology is further described elsewhere; for example, in *Fossil Fuel Emissions Control Technologies*, Bruce Miller, 2015.

Carbon dioxide may optionally be removed at this stage. Additionally, or alternatively, carbon dioxide may be removed after combining at least two different synthesis gas streams.

In one embodiment, the plant may comprise two separate Rectisol™ absorber columns that contact the synthesis gas stream with methanol comprising a common methanol regeneration system. The first absorber column may selectively remove sulphur and uses a $CO_2$ saturated solvent to minimise $CO_2$ absorption in the sulphur removal column. The second absorber column may recover $CO_2$.

This arrangement allows for the selective removal of sulphur from the synthesis gas, followed by the subsequent removal of $CO_2$. At least a portion of the resulting $CO_2$ stream may be reused in the process.

Alternatively, the clean-up process may, for example, be a chemical process such as an amine wash.

In variants of the invention which do not utilize a partial oxidation zone it is also desired to remove tars either by condensation prior to the sulphur removal bed or by using the physical absorption solvent to absorb tars and recovering them from the solvent regeneration stage.

The resulting synthesis gas is referred to herein as "clean synthesis gas".

Carbon dioxide may optionally be recovered in substantially pure form. The carbon dioxide may for example be essentially sulphur free.

At least a part of the recovered substantially pure carbon dioxide may optionally be sequestered. Sequestering carbon dioxide may involve separating, compressing, and transporting carbon dioxide to an appropriate geologic formation, where it is injected and stored permanently underground.

Additionally, or alternatively, at least a part of the recovered carbon dioxide may optionally be used for upstream and/or downstream processes, with minimal clean up required.

Carbon dioxide produced may also contribute to the carbon intensity and economics of the overall process. The source and the nature of the carbon dioxide produced will affect the carbon intensity of the process.

For example, at least part of the recovered carbon dioxide may be used to produce a low-carbon synthesis gas, for example via a reverse water gas shift (RWGS) process.

In a RWGS process, the conversion of carbon dioxide takes place in the presence of hydrogen. Preferably, the hydrogen is provided by at least a portion of the electrolysis hydrogen from the electrolyser and/or separate green hydrogen stream. The combination of recovered carbon dioxide and electrolytically derived hydrogen can have a significant impact on the carbon intensity of the overall process, for example by efficiently utilising potential carbon dioxide emissions the environmental impact may be significantly reduced.

Accordingly, in one embodiment at least a part of recovered carbon dioxide from the process and electrolysis hydrogen may be supplied to a RWGS unit wherein the carbon dioxide is converted to carbon monoxide and water.

The resulting effluent stream may be sent to upstream and/or downstream processes.

For example, the effluent stream may be combined with at least a portion of clean synthesis gas and/or reforming-derived synthesis gas and/or partially oxidised synthesis gas and/or electrolysis hydrogen, in an amount to achieve the desired $H_2$:CO molar ratio.

The resulting effluent stream from the RWGS unit may comprise a carbon monoxide and hydrogen in a $H_2$:CO ratio of between 0 and 3.

As a by-product of the RWGS process, water is produced that may be fed into upstream process, for example the electrolyser.

Advantageously, this maximizes the use of the plant facility and makes use of the $CO_2$ recovered, thus improving the carbon intensity and self-sufficiency of the plant facility.

As another non-limiting example, when natural gas is used as the feedstock for the reforming process, any carbon dioxide formed will have a fossil origin. Alternatively, carbon dioxide formed from biogas is a result of the biodegradation of green waste or agro-food waste and therefore has no fossil origin. There would therefore be no additional fossil carbon dioxide formed or greenhouse gas emissions to the atmosphere when carbon dioxide is formed from a renewable source thereby improving the carbon intensity of the overall process.

The raw synthesis gas derived from reforming may contain substantially lower concentrations of $CO_2$ than waste derived synthesis gas. The synthesis gas produced from the reforming reaction may optionally be combined with the waste derived synthesis gas after the waste derived synthesis gas has undergone $CO_2$ removal using a process as described above, for example the $CO_2$ stream may be reused in the process and/or sequestered. At least a portion of $CO_2$ from the waste derived synthesis gas may be removed prior to combining with the synthesis gas derived from reforming.

In addition, or alternatively, at least a portion of the resulting $CO_2$ stream of the blended synthesis gas (i.e. waste derived synthesis gas and synthesis gas derived from reforming) may be reused in the process and/or sequestered. The blended synthesis gas and/or the synthesis gas derived from reforming may undergo $CO_2$ removal.

Removal of $CO_2$ from the blended synthesis gas and/or the synthesis gas produced from reforming may have significant impact on the carbon intensity of the process and improving the overall economics of the facility.

The process according to the above embodiment of the present invention therefore provides a lower emissions route to a useful product when compared to a process that solely utilises solely waste derived synthesis gas.

Conventionally, a water gas shift (WGS) reaction follows a reforming process.

However, in preferred embodiments the process of the present invention may omit a separate water gas shift reaction.

It has been found that the process according to the present invention (i.e. a co-fed plant) has a higher carbon and thermal efficiency when compared to a plant that is solely fed waste.

Conventionally, an air separate unit may be used to as a feed to the gasification zone. However, in preferred embodiments that process of the present invention may omit a separate air separation unit.

It has been found that the process according to the present invention (i.e. an integrated gasification and electrolysis process) enhances the carbon intensity score when compared to conventional processes. For example, electrolysis oxygen integration within the plant facility maximises the utility of the electrolyser, optimises the overall process and eliminates the requirement of an air separation unit.

It has been found that by employing the integrated arrangement of the present invention the carbon intensity can be reduced sufficiently to allow the rest of the plant facility to be simplified, thereby benefitting the economics of the process.

Furthermore, it has been found that suppling at least one renewable source of hydrogen, preferably substantially pure hydrogen helps in obtaining specific hydrogen to carbon monoxide feed ratios and simplifying the overall process.

Advantageously, it has been found that a process according to the present invention has the ability to utilise a wide variety of different feedstocks with varying compositional characteristics. It has therefore been found that in the production of a useful product, i.e. renewable transportation fuel, a combination of renewable feedstocks may be used.

For example, the feedstock, preferably renewable feedstock, fed to the plant may comprise at least one of waste, bio-feed, green electricity, green hydrogen and/or renewable natural gas. The feedstock may be supplied as the same, or different, feed within the plant facility.

The process according to the invention may comprise at least 2 different renewable feedstocks, at least 3 different renewable feedstocks or at least 4 different renewable feedstocks.

It has been found that combining a variety of different feedstocks can be used to control the $H_2$:CO ratio to obtain the desired ratio for manufacturing the useful product. Combining different feedstocks additionally optimises the overall process and increases the plant's self-sufficiency, particularly when the feedstock is dependent on external factors. Thus, the ability to combine different feedstocks is particularly important when utilising renewable sources.

For example, green utility costs vary considerably as a consequence of external factors. For example, green electricity, such as wind power and solar energy, are produced in fluctuating amounts dependent on measurable external factors. The fluctuation in amount of green electricity produced may not correlate with demand and therefore results in shortages and surpluses that significantly effects pricing and thus economic benefit.

Additionally, or alternatively, the price of waste composition may vary significantly depending on season. The process according to the present invention implements standard measuring and sampling equipment, as well as macro-economic data, to optimise feed ratios and maintain a constant synthesis gas volume and composition.

The process of the invention is therefore configurable to control the carbon intensity of the process responsive to other, often external, factors and advantageously provides a more cost-effective and optimised route to the manufacture of a useful product.

The products formed by a process according to the first and/or second aspect of the present invention may for example constitute cleaner versions of fuels formed by conventional processes, i.e. renewable fuel.

Also provided herein is a plant configured to operate the process according to the first and/or second aspect of the present invention. Preferably, the plant is an integrated gasification, electrolysis and conversion plant.

Also provided herein is a useful product produced by a process according to the first and/or second aspect of the present invention.

For avoidance of doubt, all features relating to the process for manufacture of a useful product having a desired hydrogen to carbon monoxide molar ratio, also relate, where appropriate, to the plant configured to operate the process and vice versa.

BRIEF DESCRIPTION OF THE DRAWINGS

Preferred embodiments of the invention are described below by way of example only with reference to FIGS. 1 and 2 of the accompanying drawings, wherein.

DETAILED DESCRIPTION

Figure 1:
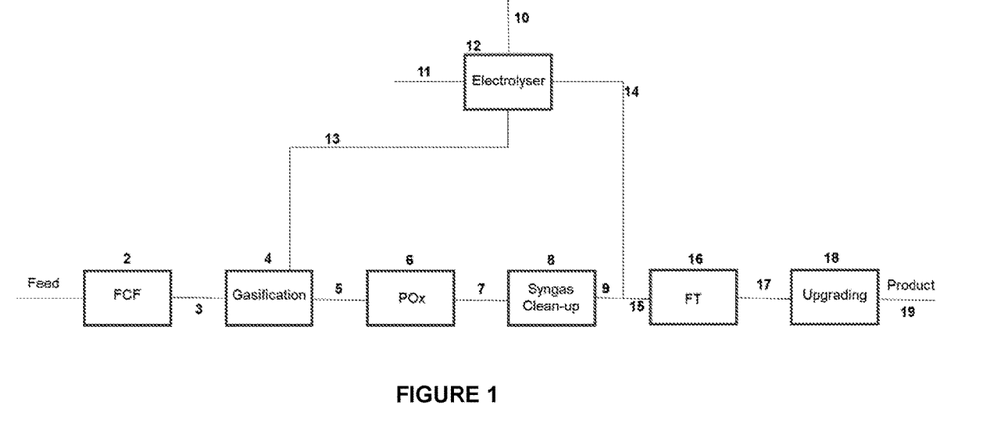
FIG. 1 is a simplified schematic diagram of a process for undertaking FT synthesis by the integration of an electrolyser with a gasification zone to in accordance with the present invention.

Referring to FIG. 1, a first carbonaceous feedstock is supplied in line 1 to Fuel Conditioning Facility (FCF) 2 and on in line 3 to gasification zone 4. Raw synthesis gas from gasification zone 4 is passed in line 5 to partial oxidation zone 6. Partially oxidised raw synthesis gas passes on in line 7 to gas clean-up zone 8, generating clean synthesis gas in line 9.

Electricity and water are supplied in lines 10 and 11 respectively to the electrolyser 12. Several different sources of electricity could be considered for electrolyser 12, with the most preferable being green electricity, for example solar or wind. Electrolysis oxygen from electrolyser 12 is passed in line 13 to gasification zone 4. It is possible in some embodiments to solely use electrolysis oxygen to supply the gasification zone 4 without the need for a separate air separation unit. If electrolysis oxygen supply is limited, it is possible that some ASU oxygen is included in order to meet the gasification zone 4 requirements.

Electrolysis hydrogen from electrolyser 12 is passed in line 14 to combine (line 15) with the clean synthesis gas from line 9. All or a portion of the blended synthesis gas in line 15 is fed to Fischer-Tropsch (FT) reactor train 16 and the resulting FT products are fed in line 17 to upgrading zone 18, generating a useful product stream in line 19.

Means are provided, for controlling the amount of electrolysis hydrogen that is combined with the waste or biomass derived synthesis gas from clean-up zone 8.

This embodiment involves the supplementing of waste-derived synthesis gas (which has a low $H_2$:CO ratio of approximately 1.0 when leaving partial oxidation zone 6) with pure electrolysis hydrogen from the electrolyser 12. Thus, the low $H_2$:CO ratio synthesis gas from waste gasification is combined with pure electrolysis hydrogen from the electrolyser 12 to produce a syngas that meets the $H_2$:CO of approximately 2.00 requirement for Fischer-Tropsch synthesis.

This embodiment preferably involves the use of green electricity and water through electrolysis to produce green hydrogen and oxygen which is used in downstream and/or upstream processes. There are several Carbon Intensity (CI) benefits arising from this scheme including:
a) if green power is used as the electricity source 10, such as solar or wind, the resulting hydrogen and oxygen will be considered "green" and thus enhances the overall CI score of the plant;
b) the integration of electrolysis oxygen into the gasification zone the utility of the electrolyser 12 is maximized and eliminates the need for an additional air separation unit (ASU)
c) the use of pure electrolysis hydrogen generated by electrolyser 12 is able to balance the $H_2$:CO molar ratio of the synthesis gas out of the partial oxidation zone ($H_2$:CO~1) to achieve the desired ratio of approximately 2, for example where Fischer-Tropsch synthesis is desired.

Figure 2:
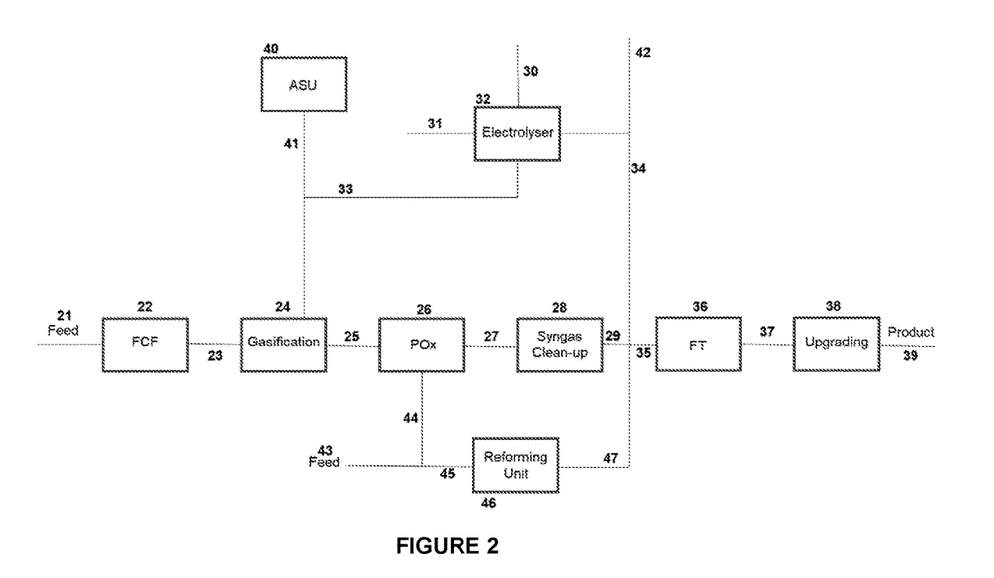
FIG. 2 is a simplified schematic diagram of a variant of the process of FIG. 1 further including the integration of a reforming unit.

In the embodiment of FIG. 2, a first carbonaceous feedstock is supplied in line 21 to Fuel Conditioning Facility (FCF) 22 and on in line 23 to gasification zone 24. Raw synthesis gas from gasification zone 24 is passed in line 25 to partial oxidation zone 26. Partially oxidised raw synthesis gas passes on in line 27 to gas clean-up zone 28, generating clean synthesis gas in line 29.

Electricity and water are supplied in lines 30 and 31 respectively to electrolyser 32. Electrolysis oxygen from electrolyser 32 is passed in line 33 to gasification zone 24. Optionally, air separation unit (ASU) oxygen from air separation unit 40 is passed in line 41 to combine (line 42) with electrolysis oxygen. At least a portion of electrolysis hydrogen from electrolyser 32 is passed in line 34 to combine (line 35) with the clean synthesis gas from line 29. Optionally, at least a portion of green hydrogen from a separate feed is supplied in line 42 and combined with electrolysis hydrogen (line 34) and/or clean synthesis gas (line 29) and/or reforming-derived synthesis gas (line 47).

A second carbonaceous feedstock may be supplied in line 43 to partial oxidation zone 44. Additionally, or alternatively, the second carbonaceous feedstock is supplied in line 45 to reforming unit 46, which may be a steam-methane reformer or an autothermal reformer. Several different feedstocks could be considered for the reforming unit 46, with the most common being natural gas. Renewable Natural Gas (RNG) is the preferred feedstock. Raw synthesis gas from reforming unit 46 is passed in line 47 to combine (line 35) with the clean synthesis gas from line 29 and/or the electrolysis hydrogen from line 34 and/or the green hydrogen from line 42. All or a portion of the blended synthesis gas in line 35 is fed to Fischer-Tropsch (FT) reactor train 36 and the resulting FT products are fed in line 37 to upgrading zone 38, generating a useful product stream in line 39.

Means are provided, for controlling the amount of electrolysis hydrogen that is combined with the waste or biomass derived synthesis gas from clean-up zone 18 and/or synthesis gas derived from reforming unit 26.

This embodiment involves the supplementing of waste-derived synthesis gas (which has a low $H_2$:CO ratio of approximately 1.0 when leaving partial oxidation zone 26) with pure electrolysis hydrogen from electrolyser 32 and/or green hydrogen from line 42 and/or raw synthesis gas from reforming unit 47, which is hydrogen rich. Thus, the low $H_2$:CO ratio synthesis gas from waste gasification is combined with pure electrolysis hydrogen from the electrolyser 32 to produce a syngas that meets the $H_2$:CO=2.00 requirement for Fischer-Tropsch synthesis.

There are several Carbon Intensity benefits arising from this scheme including:
a) the scheme allows for the utilisation of a combination of different feedstocks in the production of renewal fuels, for example, waste, bio-feed, green electricity, green hydrogen and/or green (renewable) natural gas
b) the use of a combination of different feedstocks with different compositional characteristics allows the skilled person to control the desired $H_2$:CO ratio, for example ensuring the $H_2$:CO ratio is approximately 2 where the reaction is Fischer-Tropsch
c) the use of a combination of different feedstocks with different compositional characteristics and sources reduces the constraints on an individual feedstock which may vary significantly in composition (for example waste) or in volume (for example electricity)
d) the use of a combination of different feedstocks maximizes the overall profitability and minimises feedstock costs of the overall process in variety of different ways, for example
  i) green utility costs can vary considerably. For example, green electricity (for example, wind and solar) is produced in fluctuating amounts dependent on measurable external factors. These fluctuations may frequently be out of sync with customer demand, which in turn results in shortages and surpluses that drive significant swings in pricing, which is undesirable.
  ii) waste composition and pricing varies depending on the season and is source dependent.

The scheme according to the invention utilises standard measuring and sampling equipment, as well as macroeconomic data, to optimize feed ratios and to maintain a constant syngas volume and composition.

The invention claimed is:

1. An integrated process for the production of a useful liquid hydrocarbon product comprising the steps of:
   feeding a gasification zone with an oxygen-containing feed and a first carbonaceous feedstock comprising waste materials and/or biomass,
   gasifying the first carbonaceous feedstock in the gasification zone to produce a first synthesis gas,
   partially oxidising the first synthesis gas in a partial oxidation zone to generate partially oxidised synthesis gas,
   combining at least a portion of the first synthesis gas and/or the partially oxidised synthesis gas and at least a portion of electrolysis hydrogen obtained from an electrolyser in an amount to achieve a desired hydrogen to carbon monoxide molar ratio of from about 1.5:1 to about 2.5:1, which is higher than that of the first synthesis gas, and to generate a blended synthesis gas, wherein the electrolyser operates using green electricity; and
   subjecting at least a portion of the blended synthesis gas to a conversion process effective to produce the liquid hydrocarbon product.

2. The process according to claim 1 wherein the oxygen-containing feed comprises electrolysis oxygen obtained from the electrolyser.

3. The process according to claim 1 wherein at least a portion of the first synthesis gas and/or partially oxidised synthesis gas is decontaminated in a clean-up zone to generate clean synthesis gas.

4. The process according to claim 3 wherein the clean-up zone comprises the removal of ammoniacal, sulphurous and carbon dioxide impurities.

5. The process according to claim 1 wherein the desired hydrogen to carbon molar ratio of the blended synthesis gas is from about 1.7:1 to about 2.2:1.

6. The process according to claim 1 wherein the useful liquid hydrocarbon product is produced by subjecting at least part of the blended synthesis gas to a Fischer-Tropsch synthesis.

7. The process according to claim 1 wherein the liquid hydrocarbons are upgraded into the useful liquid hydrocarbon product.

8. The process according to claim 1 wherein at least a part of the liquid hydrocarbons are upgraded by at least one of hydroprocessing, product fractionation, hydrocracking and/or hydroisomerisation to produce the useful product.

9. The process according to claim 1 wherein the product comprises synthetic paraffinic kerosene and/or diesel and/or naphtha,
optionally wherein the synthetic paraffinic kerosene and/or diesel and/or naphtha is combined with another fuel component to make a transportation fuel.

10. The process according to claim 1 wherein the process is further integrated with a reforming process.

11. The process according to claim 1 wherein the process further comprises reforming a second carbonaceous feedstock to produce a second synthesis gas.

12. The process according to claim 11 wherein the reforming step is at least one of steam methane reforming and autothermal reforming.

13. The process according to claim 11 wherein the second carbonaceous feedstock comprises gas wherein the gas is at least one of natural gas, renewable natural gas, biogas, low-carbon methanol and low carbon ethanol.

14. The process according to claim 11 wherein the first synthesis gas is subjected to partial oxidation and the second carbonaceous feedstock is combusted in the partial oxidation zone.

15. The process according to claim 11 wherein the blended synthesis gas comprises combining at least a portion of the second synthesis gas with at least a portion of the partially oxidised synthesis gas and/or at least a portion of the clean synthesis gas and/or at least a portion of the electrolysis hydrogen in an amount to achieve the desired hydrogen to carbon monoxide molar ratio.

16. The process according to claim 1 wherein the process further comprises combining green hydrogen with at least one of electrolysis hydrogen and/or partially oxidised synthesis gas and/or clean synthesis gas and/or second synthesis gas.

17. The process according to claim 1 wherein the process comprises at least 2 different renewable feedstocks, at least 3 different renewable feedstocks or at least 4 different renewable feedstocks.

18. The process according to claim 17 wherein the renewable feedstock comprises waste and/or biomass and/or green electricity and/or green hydrogen and/or renewable natural gas.

19. The process according to claim 1 wherein the desired hydrogen to carbon molar ratio of the blended synthesis gas is from about 1.95:1 to about 2.05:1.

20. The process according to claim 3 wherein the clean-up zone comprises the sequential removal of ammoniacal, sulphurous and carbon dioxide impurities.

* * * * *